(12) United States Patent
Pardoel et al.

(10) Patent No.: US 8,688,231 B2
(45) Date of Patent: Apr. 1, 2014

(54) MEDICAL PROBE AND A METHOD OF PROVIDING A MEDICAL PROBE

(75) Inventors: Michel Gerardus Pardoel, Mierlo (NL); Michel Marcel Decré, Eindhoven (NL)

(73) Assignee: Sapiens Steering Brain Stimulation B.V. (NL)

( * ) Notice: Subject to any disclaimer, the term of this patent is extended or adjusted under 35 U.S.C. 154(b) by 115 days.

(21) Appl. No.: 13/304,461

(22) Filed: Nov. 25, 2011

(65) Prior Publication Data
US 2012/0136420 A1    May 31, 2012

(30) Foreign Application Priority Data
Nov. 25, 2010 (EP) .................................... 10192512

(51) Int. Cl.
*A61N 1/05* (2006.01)
(52) U.S. Cl.
USPC ......................................... 607/116; 600/373
(58) Field of Classification Search
USPC ......................................... 607/116; 600/373
See application file for complete search history.

(56) References Cited

U.S. PATENT DOCUMENTS

| | | | |
|---|---|---|---|
| 6,374,143 B1* | 4/2002 | Berrang et al. | 607/137 |
| 7,548,775 B2* | 6/2009 | Kipke et al. | 600/378 |
| 2006/0200218 A1* | 9/2006 | Wahlstrand | 607/116 |
| 2007/0123765 A1 | 5/2007 | Hetke et al. | |
| 2007/0132109 A1 | 6/2007 | Jacobsen et al. | |

FOREIGN PATENT DOCUMENTS

| | | |
|---|---|---|
| CN | 101708353 A | 5/2010 |
| WO | 2005039696 A1 | 5/2005 |

OTHER PUBLICATIONS

International Search Report and Written Opinion dated Apr. 4, 2012 for International Patent Application No. PCT/EP2011/071068.

* cited by examiner

*Primary Examiner* — Christopher D Koharski
*Assistant Examiner* — Michael Carey
(74) *Attorney, Agent, or Firm* — Morgan, Lewis & Bockius LLP

(57) ABSTRACT

A medical probe is provided that has a single longitudinally uniform interconnect that provides a connection between a distal end and a proximal end of the probe. The interconnect is obtained by forming a thin uniform film as a spiral on a wafer and subsequently applying this spiral as a helix on a base element of a medical probe. The thin film spiral is manufactured with multiple connecting wires to enable connection between an electronics module and a multiplicity of electrodes (an electrode array) at the distal end of the medical probe.

15 Claims, 9 Drawing Sheets

MEDICAL PROBE AND A METHOD OF PROVIDING A MEDICAL PROBE

CROSS-REFERENCE TO RELATED APPLICATIONS

This application claims priority to European Patent Application No. 10192512.1 filed on Nov. 25, 2010, which is incorporated herein by reference in its entirety.

FIELD OF THE INVENTION

The present invention relates to a medical probe for an implantable medical device for electrical stimulation and to a method for manufacturing such a medical probe. In particular the invention relates to a medical probe having implantable parts for a brain implantable medical device.

BACKGROUND OF THE INVENTION

Electrical stimulation therapy is a fast-growing field, largely related to the successful use of implantable electrical stimulation devices for a wide range of applications. One example application is in deep brain stimulation (DBS).

Chinese patent application publication number CN 101708353 describes a brain stimulation electrode array including a number of stimulating electrodes connected through their respective individual electrode wires to an electrode interface. The electrode wires are arranged in a film being wound as a helix along the inside of a tube (FIG. 1) between a proximal and a distant end of the probe.

The film is typically coiled as a helix to suppress currents induced by MRI fields. Because of the helical shape, the foil with wires has to be much longer than the length of the probe itself, perhaps up to 1 m. Typically, a 1 m length of film is made out of loose piece straight parts of about 10-12 cm which are electrically/mechanically connected together to form a long length. At the connection points the film sections are typically overlapped, causing different mechanical/electrical properties at the overlaps.

US 2007/0123765 describe the folding of a serpentine polymer array to achieve long straight structures suitable for mounting on long carriers. Such folds or bends are, however, prone to cracking or damage, and the bend areas are thicker so that a helix coil formed in this manner will have differences in its properties along the length of the probe tube.

The inventors of the present invention have appreciated that it would be desirable to have a probe design that could do without the limitations associated with the bends and/or the connection of multiple lengths of film as above would result in a more reliable probe structure that would not have the limitations mentioned above.

Hence it is an object of the present invention to provide a medical probe device with higher mechanical/structural stability and integrity for the coiled thin film foil than in presently known solutions and in the lengths required for the interconnect of an implantable medical probe.

SUMMARY OF THE INVENTION

An implantable neuro-stimulating devices (e.g. for Deep Brain Stimulation) consist of an implantable electronic module and a probe. The invention describes a method by which the interconnect part of such a probe can be realized out of a single thin film without mechanical connections or bends/folds. This method offers a solid and stable solution for a critical part of a neuro-stimulating device.

It would be advantageous to achieve a probe design that could enable an efficient and reliable electrical connection between the proximal and distal ends of a medical stimulation probe. In general, the invention preferably seeks to mitigate, alleviate or eliminate one or more of the above mentioned disadvantages of the present solutions singly or in any combination. In particular, it may be seen as an object of the present invention to provide a method that solves the above mentioned problems, or other problems, of the prior art.

To better address one or more of these concerns, in a first aspect of the invention a medical probe is presented wherein an interconnect provides a connection between a distal end and a proximal end of the probe. The interconnect including a thin film foil provides said connection. The foil is in the form of a uniform helix element extending from a proximal end to a distal end of the probe. Providing a uniform helix element significantly reduces the possibility of breakage or damage to the thin film foil of the interconnect during assembly of the medical probe. Further, the uniform helix element makes it easier to apply the thin film onto a base element of the medical probe, and thus will provide for a more efficient and reliable production of a medical probe as compared with the known prior art solutions.

In embodiments of the medical probe according to the invention the thin film foil is arranged on an elongate base element, such as a cylinder element, e.g. a cylindrical tube. Using a cylindrical tube as the base element achieves two objectives, the thin film foil will relatively easy allow assembly of the thin film onto the base element as a helix and the tube shape may allocate a stylet which is typically inserted when using the medical probe.

In embodiments of the medical probe according to the invention the helix foil has been produced from a foil in the form of a spiral of Archimedes that has been wound onto the base element. Using a spiral foil to form the helix is useful because a spiral may easily be produced on a flat surface as a single, long, uniform element.

In some embodiments of the medical probe according to the invention the first and second sides of the helix foil has unequal or uneven lengths. This will for example be the consequence of using a spiral thin film foil to provide the helix foil in the medical probe.

In embodiments of the medical probe according to the invention a first side of the helix foil rests on the surface of the elongate base element, while a second side of the helix foil is at a distance from the surface of the elongate base element, thereby defining a volume between the surface of the base element and the helix foil.

In embodiments of the medical probe according to the invention two thin films each having respective sets of multiple connecting wires are arranged in a cross wise manner as helixes on each other on the element. In the inventors' experience this will provide good mechanical stability of the medical probe with a sufficiently small diameter device.

In embodiments of the medical probe according to the invention a transparent overmould layer covers the thin film helix foil(s). The overmould provides protection for the foil(s) and its connecting wires, while the transparency of the overmould enables inspection of the helix foil.

In a second aspect of the invention there is presented a method for providing a medical probe according to any above embodiments where the method comprises producing the thin film foil as a longitudinally uniform element in the form of a spiral. It has turned out that a spiral is well suited to wrapping as a helix onto a base element of the medical probe.

In embodiments of the method according to the invention the spiral foil may thus be applied as a helix onto an elongate base element extending between the distal end and the proximal end of the medical probe. Using a spiral foil enables a much longer uniform thin film than in previous solutions, and enables producing the whole thin film foil of an interconnect in a medical probe as a single, uniform thin film that is also highly suited to reliable and efficient assembly of the medical probe.

In embodiments of the method according to the invention the thin film foil forming the spiral, uniform element is provided with multiple connecting wires along its length. This means that the wires are arranged in a uniform thin film, thus reducing the risk of damage to the connecting wires associated with uneven handling caused by a non-uniform thin film of the prior art technology.

In embodiments of the method according to the invention the thin film foil is laid out as a spiral of Archimedes during the production of the thin film. A spiral is a well-defined geometry that is easy to configure, e.g. by programming a work tool, into a production tool to provide a thin film production process.

In embodiments of the method according to the invention the thin film foil is manufactured on a wafer. This means that the thin film can be produced using standard size wafers and using production steps otherwise known in the field.

In embodiments of the method according to the invention the step of applying the foil onto a base element comprises applying two spiral films, each having one or more connecting wires, in a cross wise manner as helixes, on each other onto the base element. This configuration provides good mechanical stability, while still resulting in a sufficiently small diameter of the medical probe.

In embodiments of the method according to the invention, the step of applying the foil onto a base element comprises applying two spiral films next to each other. Using two films instead of a single wide film makes it generally easier to form the helixes as a wide thin film will be stiffer and harder to coil as a helix.

In embodiments of the method according to the invention a transparent overmould layer is formed so as to cover the thin film foil(s) after application onto the base element, thereby protecting the foil and its connecting wires, while allowing inspection of the thin film foil.

In general the various aspects of the invention may be combined and coupled in any way possible within the scope of the invention. These and other aspects, features and/or advantages of the invention will be apparent from and elucidated with references to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
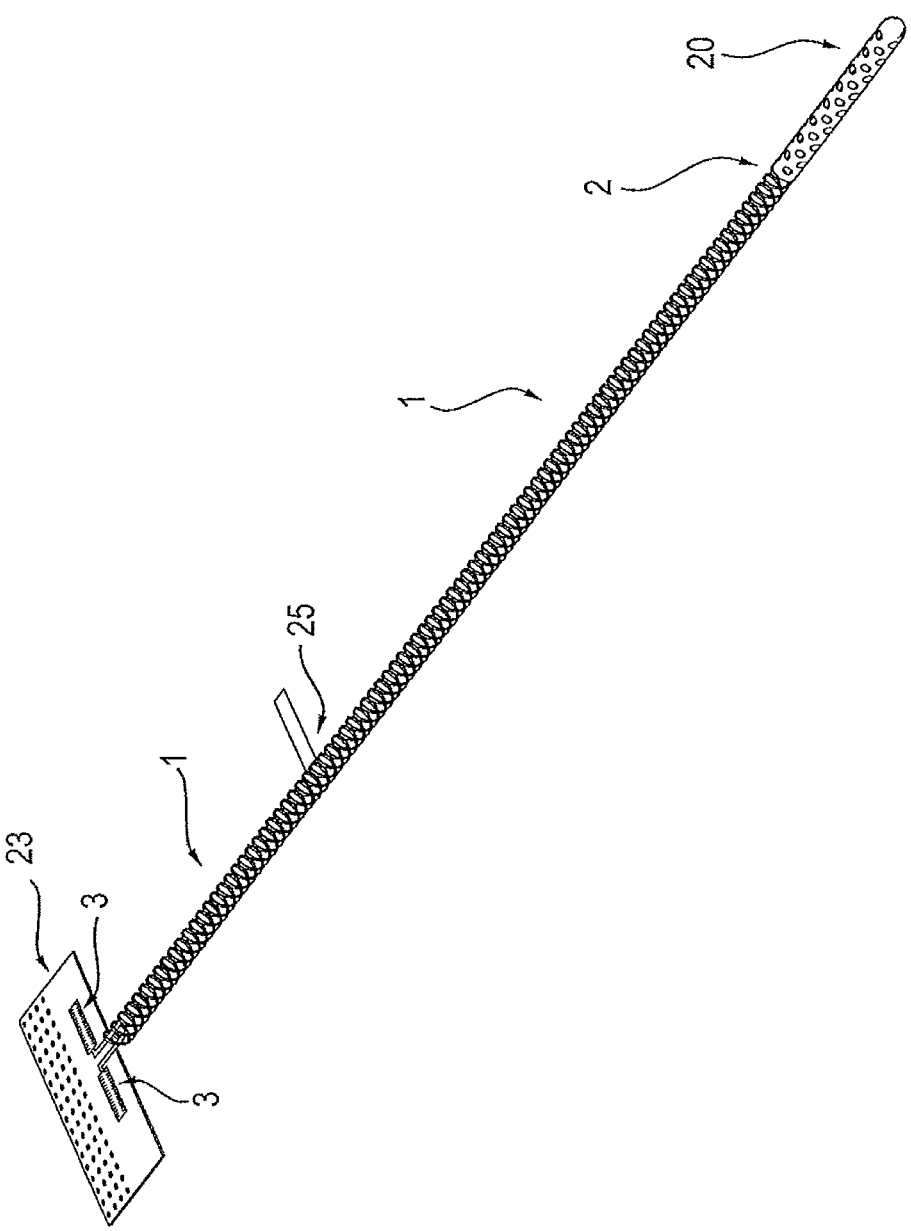
FIG. 1 shows an example embodiment of a medical probe according to the present invention in which an interconnect connects a probe interface flex with an array of stimulating electrodes.

FIG. 1 shows the chronic probe of a medical probe according to the present invention. In the addition to the chronic probe a medical probe will normally also have an electronics module (not illustrated) for creating the electrical signal for the electrodes so as to create stimulation signals. The chronic probe and the electronics module are typical parts of a medical probe according to the present invention.

The medical probe comprises an interconnect 1 that provides a connection between a distal end 2 of the chronic probe and a proximal end 3 of the chronic probe. FIG. 1 shows an array of electrodes 20 at the distal end, i.e. at the tip of the chronic probe. FIG. 1 shows a probe interface flex 23 at the proximal end 3 of the chronic probe. The interconnect 1 provides a connection between the array of electrodes 20 and the probe interface flex 23. The interconnect 1 includes a thin film foil 4 that has multiple connecting wires 5 providing an electrical connection between the proximal 3 and distal 2 ends of the medical probe. The electrode array 20, the interconnect 1 and the probe interface flex 23 may be made of flat parts (thin film or flex) and may be connected to each other by the use of riveting (balls contacts).

Figure 2:
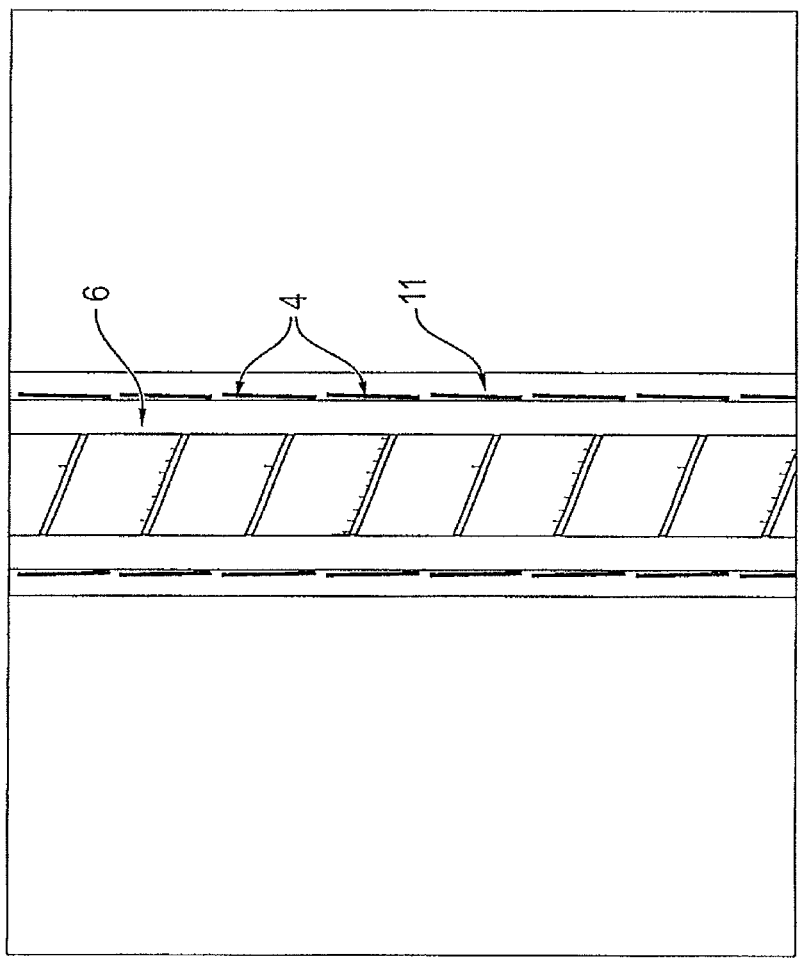
FIG. 2 shows a detailed longitudinal section of an interconnect in an example embodiment of a medical probe according to the present invention.

FIG. 2 illustrates in more detail a longitudinal section of the interconnect 1 between the electrode array 20 and the probe interface flex 23. The interconnect 1 comprises one or more thin spiralised films 4 applied as helixes on an elongate base element 6, e.g. a cylinder element such as a cylinder tube. The elongate base element 6 may be made of silicone, with an inner diameter of about 0.6 mm and with an outer diameter of about 1 mm. In an example embodiment of the medical probe according to the invention two spiralised thin films 4 are wrapped helically onto the base element 6.

Figure 3:
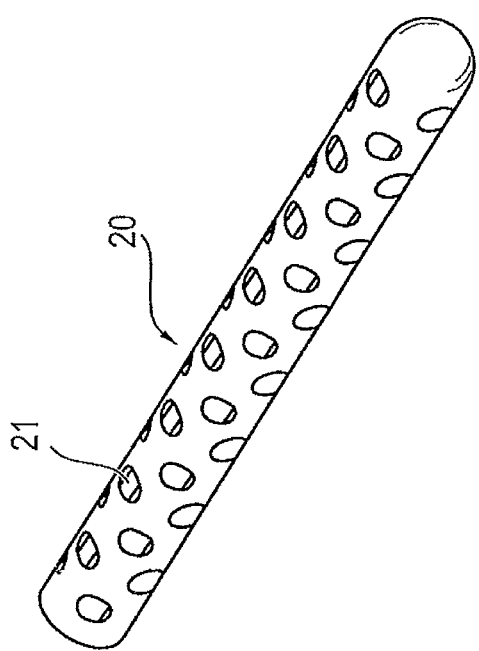
FIG. 3 illustrates in more detail an example of an electrode array in an example embodiment of a medical probe according to the present invention.

FIG. 3 illustrates an example of the electrode array 20 locations of the medical probe. As an example, there may be 64 electrodes 21 distributed evenly on the surface of the electrode array 20. The electrode array 20 may be produced from a flat thin film part with stimulating sites defined by the stimulating electrodes 21 laid out on the flat thin film part.

Figure 4:
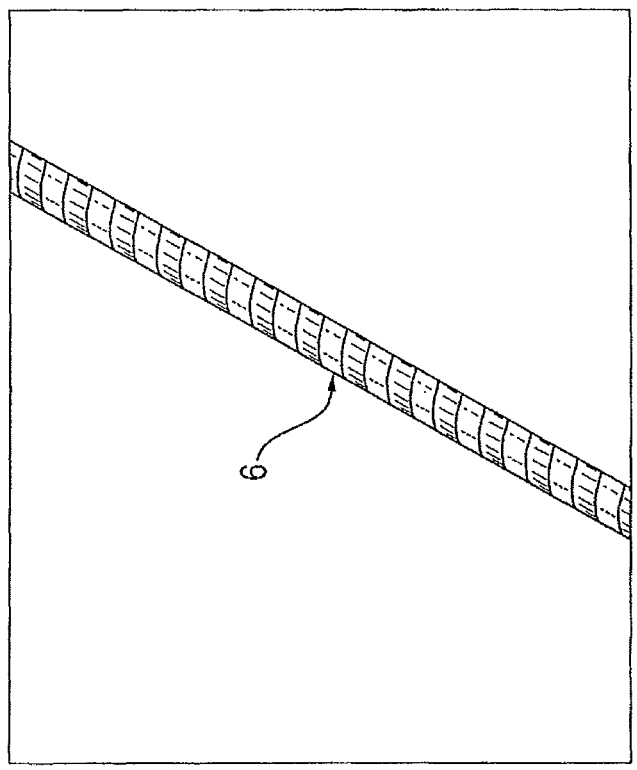
FIG. 4 shows a detailed example of an interconnect in an example embodiment of a medical probe according to the present invention

FIG. 4 illustrates how a base element 6 of the medical probe according to the invention may also be provided by coiling flat elements into a base element having a tubular structure. Consequently, most parts of the interconnect, the electrode array, and the probe interface flex of the medical probe may be manufactured as flat, thin elements that are formed into their final shapes.

Figure 5:
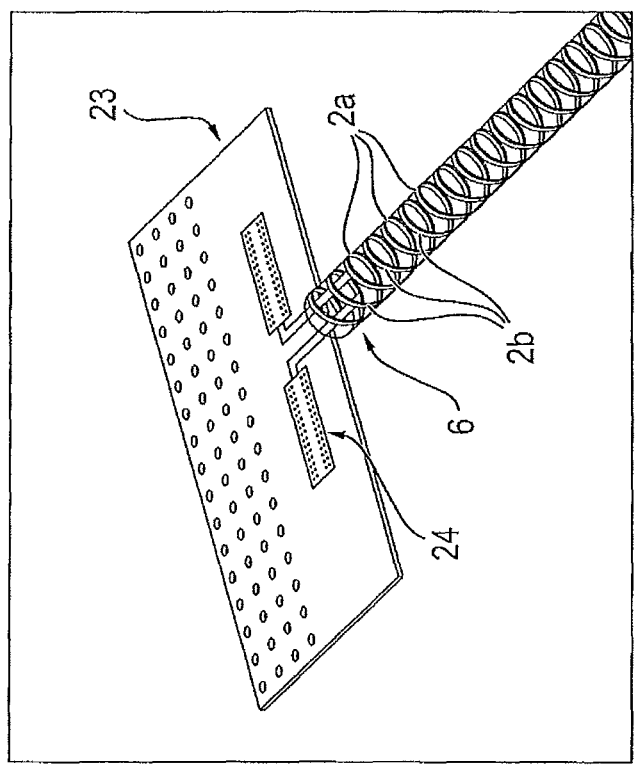
FIG. 5 shows an example detail of termination of an interconnect in a probe interface flex of an example embodiment of a medical probe according to the present invention.

FIG. 5 illustrates in more detail the probe interface flex 23 and the connection to the interconnect 1. The probe interface flex 23 provides the connection between the interconnect 1 and the stimulating electrodes 21. The probe interface flex 23 may be realized as a flat flex or as a flat thin film. The thin film spiral foil 4 is wrapped as a helix to form the interconnect 1, the helix starting at a proximal end 3 of the probe and being connected to the probe interface flex 23 by for example riveting, i.e. as ball contacts. At the distal end 2 the thin film 4 is connected to the stimulating electrodes 21.

In the experience of the present inventors two thin films of relatively lower width are easier to form into helixes than a single relatively wider thin film, due to the width of a single film creating a significantly stiffer structure that is more difficult to wrap onto the base element. At both ends of the interconnect 1 there are provided contact areas. In the case of using two helical thin films 2 times 32 contacts are used. In the present inventors' experience it is easier to make 32 contacts in two steps than the full set of 64 contacts in one go. The helical thin films of the interconnect 1 may be connected to the electrode array 20 by riveting, i.e. as ball contacts.

In order to make it possible to operate the medical probe according to the invention in magnetic resonance (MR) environments the multiple connecting wires of the thin film(s) 4 should be wound as a spiral or helix. In this way the medical probe will not significantly affect the quality of diagnostic information obtained in the MR-process, nor will the operation of the medical probe be significantly affected by the MR-environment.

The length of the interconnect 1 itself is usually several centimeters, normally in the range of 6-15 cm, and typically about 10 cm, however, when the thin film is wrapped as a helix the required length of the thin film is about 1 m. The present invention enables the manufacturing of long lengths of single, longitudinally uniform thin films 4 that can be wound as a helix on a base member to create the interconnect of a chronic probe. Thin films of about 1 m length are provided as part of the present invention. The multiple connecting wires that provide the electrical connection between the electrode array 20 and the probe interface flex 23 may be realized as tracks on the long thin films 4 during manufacture of these.

Long lengths of thin film foils 4 that may be wrapped as a helix onto an elongate element 6 are known in the prior art, either using the technique of connecting many short straight pieces or by the technique of bending a meandered part into a straight section. However, as has been explained in the introduction the bends and/or connection areas become stiffer than the remaining parts of the thin film, making the film difficult to arrange in a good helix, and the films made using such prior art techniques are prone to cracking or damage at the stiffer sections, thus risking loosing the connection. With the medical probe according to the present invention these limitations are avoided, due to the longitudinally uniform structure of the thin films.

Figure 6:
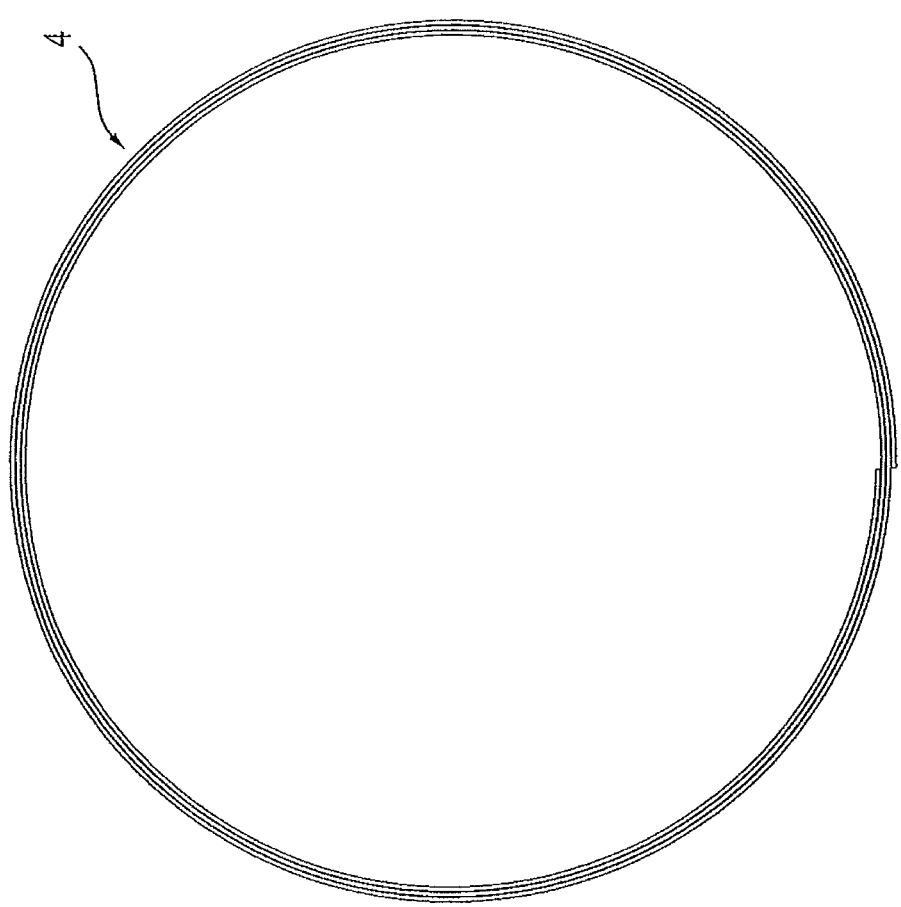
FIGS. 6-7 illustrate the full spiral thin film and a segment of the spiral film, respectively, before being applied as a helix on an elongate base element to form the interconnect.
Figure 7:
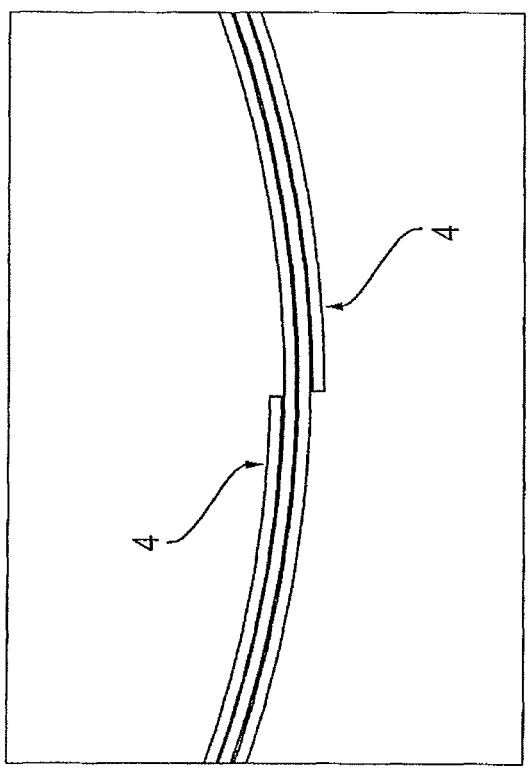

The present inventors have realized that it is possible to create a spiral film, as exemplified on FIGS. 6-7, on a flat surface, such as a wafer and then wrapping this film as a helix onto the elongate base element 6 of the chronic probe. The present inventors have experienced that it is in fact possible to wrap this spiral onto the elongate element 6 and apply an overmould 11 after wrapping the film 4 as a helix onto a base element 6. The present inventors have experienced that it is perfectly possible to apply an initially flat, spiral film as a helix on a base element and then apply a protecting overmould 11 without moving or damaging the thin film 4 in the operation even though the film does not lie flat on the cylinder surface. The initially flat, spiral film could for example be shaped as a spiral of Archimedes. Although FIGS. 6-7 show a single spiral length, a number of spirals may be produced in a concentric, sequential, manner where an inner spiral of low radius is surrounded by a number of additional spirals of gradually larger radius. This means that spirals may be produced in a very effective manner, in so far as a number of spirals may be produced on a single wafer.

Figure 8:
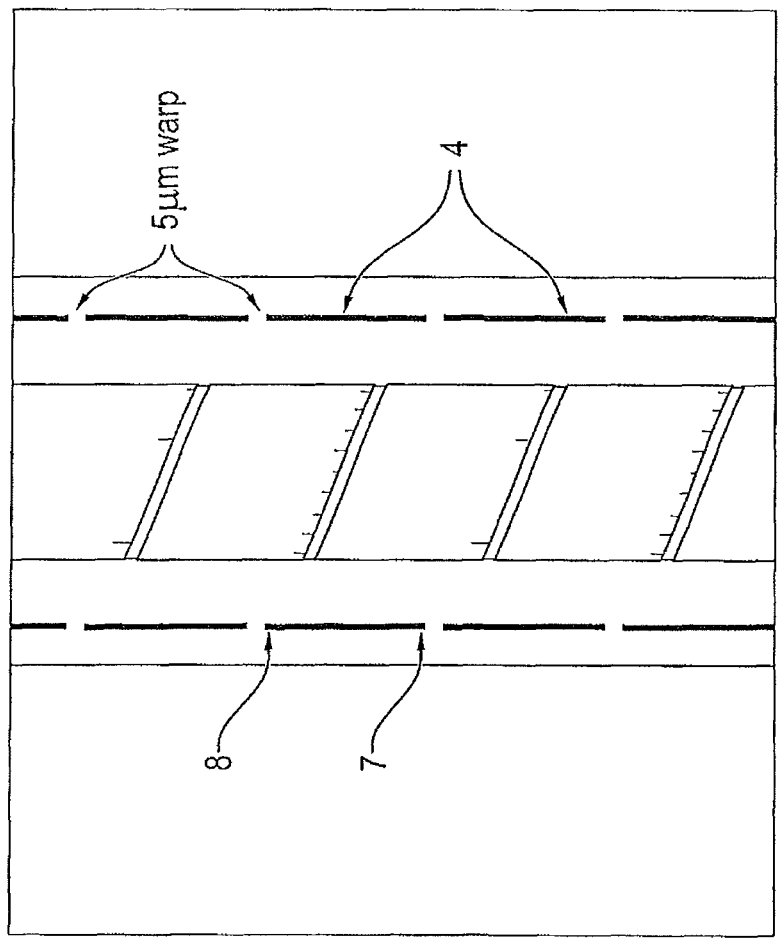
FIGS. 8-9 illustrate a thin film foil helix with warps of 5 µm and 21 µm, respectively, in an interconnect of an example embodiment of the present invention.
Figure 9:
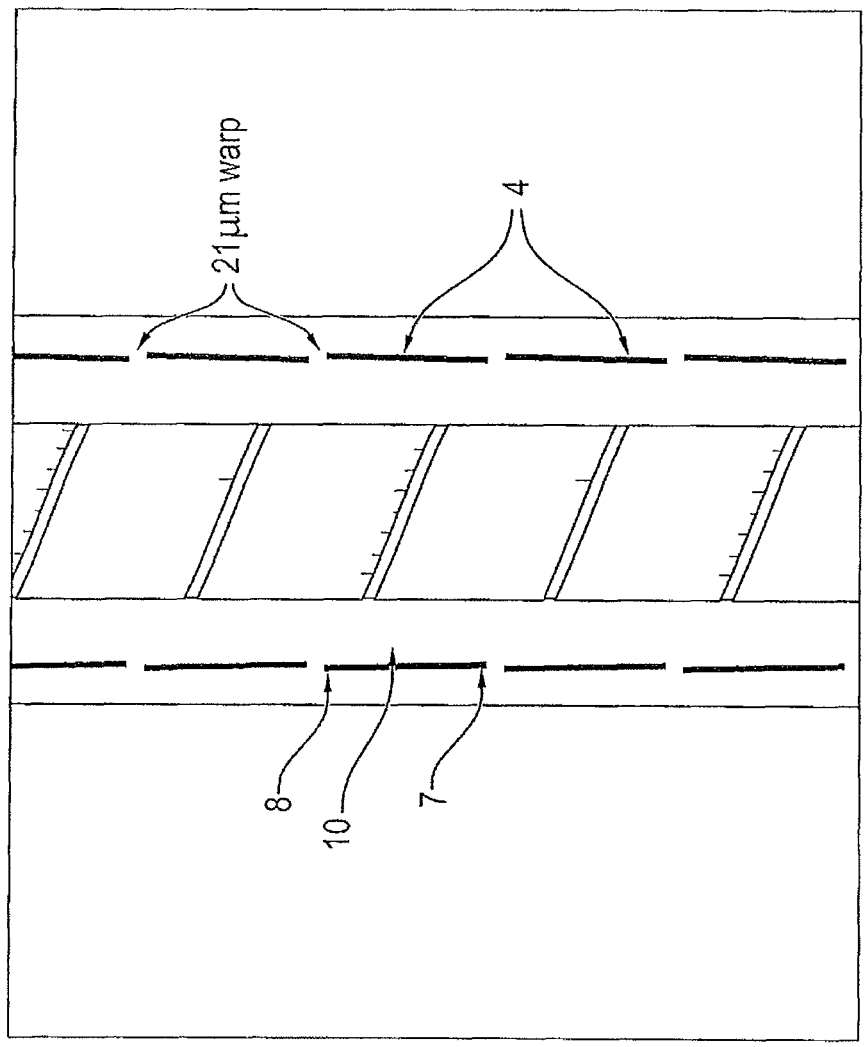

FIGS. 8-9 illustrate a longitudinal cross section of the interconnect 1 of the medical probe. The elongate base element 6 may be a base tube made of silicone onto which the thin film(s) are arranged in a helical fashion along the length of the base element to form an interconnect. A silicone overmould 11 is applied over the thin film(s) and silicone base tube to make the interconnect robust and stable. The overmould could be made from a biocompatible material, otherwise known in the art. In the overmould a stylet entrance 25 is provided to enable insertion of a stylet into the base element 6. A stylet is needed to stiffen the probe during insertion of the probe into a tissue to be stimulated, for example brain tissue.

FIGS. 8-9 also illustrate that when starting the thin film wrapping from a flat, spiral thin film a first longitudinal edge 7 of the thin film 4 will—when mounted on the base element—be in contact along its length with the surface of the elongate base element 6 (the silicone base tube), while the second longitudinal edge 8 of the thin film will be raised a distance away from the surface of the base element 6. The raised thin film 4 may be denoted a warp or warping. In this way a longitudinally uniform thin film 4 without bends or connections along the interconnect may be realized with a warp. This may be regarded as a simplification of the process of making such a medical probe, as the operations of multiple bending or gluing/connecting of sections of thin film containing wires are reduced to a minimum, in fact it may be completely avoided.

FIGS. 8-9 illustrate helical thin films with 5 μm warp and 21 μm warp, respectively. This novel technique of wrapping a thin film spiral around an elongate base element while maintaining the possibility of overmoulding can also be done by laying two spirals crosswise to obtain even better MRI compatibility.

In a second aspect of the invention there is provided a method for providing a medical probe with an interconnect 1 that provides a connection between a distal end 2 and a proximal end 3 of the medical probe. A spiraled thin film foil 4 is provided by manufacturing the foil as a longitudinally uniform element in a spiraling fashion on a flat surface, e.g. a wafer. The spiraled foil is provided with multiple connecting wires during the manufacturing of the foil, to provide an electrical connection between an electrode array 20 and a probe interface flex 23 when placed in the medical probe. The foil 4 is applied as a helix onto an elongate base element extending between said distal end and said proximal end of the probe.

FIG. 6 illustrates an example of a single complete thin film spiral according to the invention, for example as manufactured on a flat wafer. FIG. 7 illustrates in more detail a part of the thin film spiral while still on the surface of the wafer.

One example embodiment of the medical device according to the present invention is a deep brain stimulation probe, where the array of electrodes 21 is provided at the distal end 2 of the probe and is connected by respective connecting wires to a probe interface flex 23 at the proximal end 3 of the probe. The connecting wires connecting with the electrodes are a part of a thin film foil 4. The thin film spiral foil 4 is removed from the wafer and wound as a helix on an elongate element 6, e.g. a cylindrical tube forming the base element 6 of the probe.

In the method according to the invention the three main parts: the electrode array 20, the interconnect 1 and the probe interface flex 23 may be put together as follows: The array electrode 20 is wrapped around the elongate base element 6 in the form of a base tube. Typically, the base tube is made from silicone and has an inner diameter of about 0.6 mm and an outer diameter of about 1 mm. Then the thin film spiral 4 is wrapped as a helix to create the interconnect 1 (one or two thin films). After the fixing of the thin film 4 to the base tube 6, an overmould 11 of a suitable material, such as silicone, is applied over the tube and the thin film.

In embodiments of the method according to the invention a stylet entrance 25 is formed as part of the step of overmoulding. The stylet entrance is formed so as to provide easy and reliable entry of the stylet into a central longitudinal hollow in the elongate base element. The stylet entrance may be produced so as to be closable after removal of the stylet.

The design of the spiral thin film 4 on the wafer will now be described in some more detail. The thin film may be manufactured as a spiral pattern on a flat surface, e.g. on a wafer. In particular, the thin film may be formed as a spiral of Archimedes on a wafer. Such a spiral consists of a number of turns with decreasing radius, which in polar coordinates may be expressed by the equation $$R(\varphi)=A+B\cdot\varphi$$

where A is the starting point and B the spacing between adjacent lines. In Cartesian coordinates the equations for such a spiral are as follows:

$$x=R(\varphi)\cdot\cos\varphi$$

$$y=R(\varphi)\cdot\sin\varphi$$

In this way, 13 films with a width of 0.556 mm and a length of at least 1 m each can be created on a 6" wafer.

The spiral thin films 4 with connecting wires are released from/taken off the wafer and wrapped as a helix on the elongate base element 6, e.g. a tube, to realize the interconnect 1 between the electrode array 20 and a connector on the probe interface flex 23 at the proximal end 3 of the probe. This is somewhat special, since due to the fact that the thin film has been prepared as a spiral of Archimedes on a wafer, the two long edges of the resulting thin film have different lengths and the thin film will therefore not lie flat on the surface of the base element. The present inventors have demonstrated/calculated that the opening/lift/distance (also denoted the warp) to the cylinder will remain sufficiently small to allow fabrication and overmoulding of the wrapped film.

FIG. 6 shows a spiral on a wafer and FIG. 7 gives a detail of this spiral. The wafer is typically a 6" (152.4 mm) wafer. This thin film spiral 4 may be removed from the wafer to create a loose piece spiral. The outer inch on the wafer is left free, so the starting diameter is 5" (=127 mm). The drawn spiral has a width of 556 μm; the pitch between 2 adjacent spiral lines is 700 μm. Table 1 gives a calculation for spirals on one wafer. It seems possible to realize 13 spirals on one wafer. It will be evident to a person skilled in the art that this method will result in an increased efficiency in production as compared to previously known techniques. Because two films are often desirable for a single probe it is attractive to manufacture twelve spirals on one wafer, creating a batch of six sets of interconnects from one wafer. All spirals may have connection areas at both ends. Because of this the layout on the wafer may have other dimensions.

TABLE 1 spiral parameters

| spiral # | n (turns) | outer diameter | delta diameter | average diameter | spiral length |
|---|---|---|---|---|---|
| 1 | 3 | 127 | | 124.344 | 1171.914591 |
| 2 | 3 | 121.4 | 5.6 | 118.744 | 1119.135834 |
| 3 | 3 | 115.8 | 5.6 | 113.144 | 1066.357078 |
| 4 | 3 | 110.2 | 5.6 | 107.544 | 1013.578321 |
| 5 | 4 | 104.6 | 5.6 | 101.244 | 1272.269626 |
| 6 | 4 | 97.6 | 7 | 94.244 | 1184.305032 |
| 7 | 4 | 90.6 | 7 | 87.244 | 1096.340438 |
| 8 | 4 | 83.6 | 7 | 80.244 | 1008.375844 |
| 9 | 5 | 76.6 | 7 | 72.544 | 1139.518487 |
| 10 | 5 | 68.2 | 8.4 | 64.144 | 1007.571596 |
| 11 | 6 | 59.8 | 8.4 | 55.044 | 1037.554956 |
| 12 | 8 | 50 | 9.8 | 43.844 | 1101.919906 |
| 13 | 11 | 37.4 | 12.6 | 29.144 | 1007.144339 |
| | | 20.6 | 16.8 | 20.044 | |

With the example of Table 1 all spirals will have a length of at least 1 m. All spirals have a whole number of turns. There is one pitch left between two spirals, so the first spiral of the two spirals lies between a first outer diameter of 127 mm and a second outer diameter of 121.4 mm. The respective spiral lengths are calculated with the average diameters.

When a straight thin film is wrapped around an elongate base element such as a base tube with a certain pitch the whole film has contact with the tube. This is not the case when a spiral thin film is wrapped around the base tube. When the spiral thin film is wrapped around the base tube on its inner diameter, it is possible to calculate the distance of the free outer diameter from the surface of the base tube (stress free situation; only the bending stress of the wrapping process) and the angle that the spiral film makes with the base tube. As an example calculation we may assume the following parameters:

Outer diameter base tube is 1 mm,

Pitch on the base tube is 1.2 mm

Width of 1 film is 0.556 mm

L1 is the length of 1 turn inner spiral radius, tightly wrapped around the base tube with the given pitch of 1.2 mm.

α is the angle over which length L1 is taken from the inner radius.

L2 is the length of this spiral part at the outer radius.

D2 is the diameter in which length L2 results after wrapping.

Delta D is the difference in diameter.

Delta R is the difference is radius.

TABLE 2 angle and gap calculations

| spiral # | L1 | α | L2 | D2 | Delta D | Delta R |
|---|---|---|---|---|---|---|
| 1 | 3.362976 | 3.099214 | 3.39305 | 1.010241 | 0.010241 | 0.005121 |
| 2 | 3.362976 | 3.245373 | 3.394469 | 1.010724 | 0.010724 | 0.005362 |
| 3 | 3.362976 | 3.406001 | 3.396027 | 1.011254 | 0.011254 | 0.005627 |
| 4 | 3.362976 | 3.583358 | 3.397749 | 1.01184 | 0.01184 | 0.00592 |
| 5 | 3.362976 | 3.806335 | 3.399912 | 1.012576 | 0.012576 | 0.006288 |
| 6 | 3.362976 | 4.089052 | 3.402656 | 1.013509 | 0.013509 | 0.006755 |
| 7 | 3.362976 | 4.417136 | 3.40584 | 1.014592 | 0.014592 | 0.007296 |

TABLE 2-continued angle and gap calculations

| spiral # | L1 | α | L2 | D2 | Delta D | Delta R |
|---|---|---|---|---|---|---|
| 8 | 3.362976 | 4.80246 | 3.409579 | 1.015864 | 0.015864 | 0.007932 |
| 9 | 3.362976 | 5.312205 | 3.414525 | 1.017546 | 0.017546 | 0.008773 |
| 10 | 3.362976 | 6.007867 | 3.421276 | 1.019841 | 0.019841 | 0.00992 |
| 11 | 3.362976 | 7.001101 | 3.430914 | 1.023116 | 0.023116 | 0.011558 |
| 12 | 3.362976 | 8.78954 | 3.448269 | 1.029011 | 0.029011 | 0.014505 |
| 13 | 3.362976 | 13.22291 | 3.491291 | 1.043606 | 0.043606 | 0.021803 |

Table 2 shows the results of these calculations for all 13 spirals.

It will be seen that spiral #1 has a distance at the outer diameter from the outside surface of the base tube of about 5 μm (see FIG. 6), while spiral #13 has a distance at the outer diameter from the outside surface base tube of about 21 μm (see FIG. 7). The outer diameter of the base tube is 1 mm. The outer diameter of the probe after overmoulding is 1.27 mm. This means that all spirals will be completely overmoulded and will result in a stable, robust and biocompatible solution.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

The invention claimed is:

1. A medical probe comprising:
an interconnect providing a connection between a distal end and a proximal end of a probe, the interconnect including a thin film foil providing said connection, the thin film foil being a uniform helix element extending from the proximal end to the distal end of the probe, the thin film having a first edge and a second edge, the second edge being longitudinally spaced from the first edge along a length of the probe, a circumferentially extending length of the first edge of the thin film foil being less than a circumferentially extending length of the second edge of the thin film foil for a complete segment of the thin film foil wrapping exactly once around the probe.

2. The medical probe according to claim 1, wherein the thin film foil is arranged on an elongate base element, such as a cylinder.

3. The medical probe according to claim 1, wherein the first edge of the thin film foil rests on a surface of an elongate base element, while the second edge of the thin film foil is spaced a distance from the surface of the elongate base element, thereby defining a volume between the surface of the base element and the thin film foil.

4. The medical probe according to claim 1, wherein the uniform helix element is non-overlapping with itself.

5. The medical probe according to claim 1, wherein the thin film foil is produced from a foil in the form of a spiral of Archimedes before being wound onto the probe.

6. The medical probe according to claim 1 further comprising:
a second thin film foil, each of the thin film foils having multiple connecting wires, arranged in a cross wise manner as helixes on each other on the probe.

7. The medical probe according to claim 1 further comprising:
a transparent overmould layer covering the thin film foil.

8. A method for providing a medical probe according to claim 1, comprising producing the thin film foil as a planar element in the form of a spiral.

9. The method according to claim 8, wherein the thin film foil is applied as a helix onto an elongate base element extending between the distal end and the proximal end of the probe.

10. The method according to claim 8, comprising manufacturing the thin film foil with multiple connecting wires along the spiral, planar element.

11. The method according to claim 8, wherein during the production of the thin film foil, the thin film foil is laid out as a spiral of Archimedes.

12. The method according to claim 8, comprising the step of manufacturing the thin film foil on a wafer.

13. The method according to claim 9, wherein the step of applying the thin film foil onto the elongate base element comprises applying two spiral films, each spiral film having one or more connecting wires, in a cross wise manner as helixes, on each other onto the elongate base element.

14. The method according to claim 9, wherein the applying the thin film foil onto the elongate base element comprises applying two spiral films next to each other.

15. The method according to claim 9 further comprising:
providing a transparent overmould layer covering the thin film foil after its application onto the elongate base element.

* * * * *